United States Patent [19]
Galey

[11] Patent Number: 6,004,543
[45] Date of Patent: Dec. 21, 1999

[54] L-2-OXOTHIAZOLIDINE-4-CARBOXYLIC ACID DERIVATIVES AND USE THEREOF FOR SKINCARE

[75] Inventor: Jean-Baptiste Galey, Aulnay-sous-Bois, France

[73] Assignee: L'Oreal, Paris, France

[21] Appl. No.: 08/771,836

[22] Filed: Dec. 23, 1996

[30] Foreign Application Priority Data

Dec. 22, 1995 [FR] France .................................. 95 15334

[51] Int. Cl.⁶ ........................... A61K 7/42; C07D 277/14
[52] U.S. Cl. ................ 424/62; 424/59; 424/63; 424/401; 510/130; 514/369; 548/188
[58] Field of Search ............. 548/188; 514/369; 424/62, 401

[56] References Cited

U.S. PATENT DOCUMENTS

| | | | |
|---|---|---|---|
| 4,774,255 | 9/1988 | Black et al. | 514/423 |
| 4,986,982 | 1/1991 | Scott | 424/63 |
| 5,045,559 | 9/1991 | Scott | 514/423 |
| 5,137,714 | 8/1992 | Scott | 424/63 |
| 5,208,249 | 5/1993 | Rowe et al. | 514/369 |

FOREIGN PATENT DOCUMENTS

| | | |
|---|---|---|
| 0 656 201 | 6/1995 | European Pat. Off. . |
| 2 139 225 | 11/1984 | United Kingdom . |

*Primary Examiner*—Mukund J. Shah
*Assistant Examiner*—Ann M. Kessinger
*Attorney, Agent, or Firm*—Oblon, Spivak, McClelland, Maier & Neustadt, P.C.

[57] ABSTRACT

The invention relates to novel compounds of formula (I):

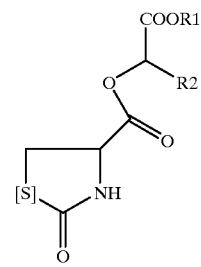

where R1 is chosen from hydrogen, saturated or unsaturated linear or branched C1 to C8 alkyl groups which are optionally substituted with a substituent, and optionally substituted benzyl groups, and R2 is chosen from hydrogen, saturated or unsaturated linear or branched C1 to C24 alkyl groups which are optionally substituted with a substituent, aromatic groups which are optionally substituted with a substituent, and saturated or unsaturated heterocyclic groups; and the use of these derivatives for skincare.

17 Claims, No Drawings

L-2-OXOTHIAZOLIDINE-4-CARBOXYLIC ACID DERIVATIVES AND USE THEREOF FOR SKINCARE

BACKGROUND OF THE INVENTION

1. Field of the Invention

The invention also relates to a use of these L-2-oxothiazolidine-4-carboxylic acid derivatives as a precursor of cysteine and of hydroxy acid. The invention also relates to uses of these L-2-oxothiazolidine-4-carboxylic acid derivatives for skincare.

2. Description of the Background

Users of cosmetic and/or dermatological products are increasingly seeking to rejuvenate the skin, i.e. reduce wrinkles and fine lines, brighten the complexion of the face and make the skin supple. These signs of ageing are not only due to age but also especially to exposure to the sun and to other radiation such as artificial tanning by UV rays in particular.

In parallel, these same users are increasingly seeking to lighten the skin.

The active agents known to combat ageing are retinoic acid and derivatives thereof. Unfortunately, these active agents have side effects, such as stinging, heating sensations and causing redness, which are unpleasant for the user and exclude users with sensitive skin from using this type of active agent.

There is thus a need for anti-ageing and/or bleaching agents that are as effective in their action as those in the prior art but that do not exhibit the drawbacks thereof.

Moreover, there are currently very few active agents having depigmenting properties.

L-2-Oxothiazolidine-4-carboxylic acid esters intended to stimulate the intracellular synthesis of glutathione in certain cells of the human body are known from U.S. Pat. No. 5,208,249. These esters comprise a group having from 1 to 10 carbon atoms and is chosen from the methyl, ethyl, propyl, isopropyl, butyl, isobutyl and tert-butyl groups.

Other L-2-oxothiazolidine-4-carboxylic acid esters used as cysteine precursors and in combination with glutathione stimulators to prevent hair loss and to stimulate the growth of new hair are moreover known from EP-A-656,201. These esters have an alkyl group of from 1 to 10 carbon atoms and is chosen from the methyl, ethyl, propyl, butyl, pentyl, hexyl, peptyl, octyl, nonyl, decyl, isopropyl, isobutyl, sec-butyl, tert-butyl and isopentyl groups.

SUMMARY OF THE INVENTION

The Applicant has discovered, surprisingly, novel L-2-oxothiazolidine-4-carboxylic acid esters which make it possible to prevent and/or combat photo-induced ageing as well as to depigment or bleach the skin without causing any skin irritation. The esters intervene in particular in the synthesis of melanin and in the removal of dead cells from the skin (or desquamation).

The subject of the invention is a compound of general formula (I)

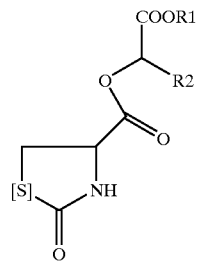

where R1 is chosen from hydrogen, saturated or unsaturated Linear or branched C1 to C8 alkyl groups which are optionally substituted with a substituent, and optionally substituted benzyl groups, and R2 is chosen from hydrogen, saturated or unsaturated linear or branched C1 to C24 alkyl groups which are optionally substituted with a substituent, aromatic groups which are optionally substituted with a substituent, and heterocyclic groups.

DETAILED DESCRIPTION OF THE INVENTION

Advantageously, R1 is chosen from saturated linear alkyl groups having from 1 to 4 carbon atoms and R2 is chosen from saturated or unsaturated alkyl groups having from 1 to 18 carbon atoms and the benzyl group.

R2 is preferably chosen from benzyl or saturated alkyl groups.

The substituent in R1 and R2 may be chosen from chlorine or fluorine atoms and OH, COOH and OR3, R3 being as defined as C1–C18 alkyl and benzyl.

The heterocyclic group may include a hetero atom chosen from nitrogen, oxygen and sulphur. This heterocycle can moreover be substituted with one of the above substituents.

Preferably, R1 is an ethyl or benzyl group and R2 is chosen from a methyl, propyl, dodecyl and benzyl group, and hydrogen.

The compound according to the invention is preferably chosen from 2-oxothiazolidine-4-carboxylic acid 1-ethoxycarbonyl ethyl ester, 2-oxothiazolidine-4-carboxylic acid 1-ethoxycarbonyl methyl ester, 2-oxothiazolidine-4-carboxylic acid 1-ethoxycarbonyl butyl ester, 2-oxothiazolidine-4-carboxylic acid 1-ethoxycarbonyl phenylmethyl ester, 2-oxothiazolidine-4-carboxylic acid 1-ethoxycarbonyl tridecyl ester and 2-oxothiazolidine-4-carboxylic acid 1-benzyloxycarbonyl ethyl ester.

Another subject of the invention is a cosmetic composition comprising at least one compound as defined above.

The subject of the invention is also a use, as a cysteine precursor and/or as a hydroxy acid precursor, of the compound of abovementioned formula (I).

Another subject of the invention is a use of an hydroxy acid and/or cysteine precursor as a depigmenting agent. The precursor may be, especially in this case, the compound of formula (I).

One of the other subjects of the invention is the use of the above compound to protect the skin against the irritation and/or sensitization caused by components which are foreign to the body, also referred to as "xenobiotics".

The subject of the invention is also a use of an hydroxy acid and/or cysteine precursor to prevent and/or combat photo-ageing of the skin. The precursor may be, in this case, the compound of formula (I).

The last two subjects of the invention are a cosmetic and/or dermatological treatment process which comprises applying to the skin the compound of formula (I) in a cosmetically or dermatologically acceptable medium, and a process for manufacturing this compound which comprises mixing the L-2-oxothiazolidine-4-carboxylic acid with an α-bromo ester, in the presence of a molar equivalent of a base, and then in heating the reaction mixture, cooling it and filtering it.

This manufacturing process is furthermore characterized by an extraction of the organic phases, their drying and then their purification. This base may be chosen from sodium hydroxide, potassium hydroxide and methanolamine.

The expression "cosmetically or dermatologically acceptable medium" is understood to refer to a medium which is compatible with the skin, the mucous membranes, the nails and the hair.

Once applied to the skin, the compound according to the invention has the advantage of providing a hydroxy acid in precursor form, as well as cysteine also in stable precursor form, the cysteine entering into the composition of glutathione.

Indeed, glutathione is composed of the following three amino acids: glutamic acid, cysteine and glycine. It is known in particular to be involved in the protection of cells against various injuries, such as those caused by free radicals (see U.S. Pat. No. 5,208,249). In addition, it allows inhibition of the production of melanin used in pigmentation of the skin.

Moreover, the compound according to the invention has a lipophilic nature which facilitates its incorporation into compositions, in particular cosmetic compositions, to form, for example, emulsions of oil-in-water or water-in-oil type. Lastly, the compound according to the invention possesses excellent qualities of penetration into the skin.

The composition according to the invention may furthermore comprise at least one additive chosen from fatty substances, preserving agents, vitamins, gelling agents, fragrances, silicones, surfactants, water, antioxidants, fillers, screening agents, moisturizers and mixtures thereof.

The fatty substances may be chosen from oils such as jojoba oil, liquid petrolatum or isopropyl palmitate, or from waxes such as sipol wax, carnauba wax, silicones, fatty acids and fatty alcohols.

The surfactant which may be present in the composition may be chosen from glyceryl mono di-stearate and sodium stearate, and the gelling agent may be chosen from polyethylene glycols which are optionally oxyethylenated.

The compound according to the invention may be present in an amount ranging from 0.01 to 10% by weight and preferably in an amount ranging from 0.5 to 5% by weight relative to the total weight of the composition.

The additive may be present in the composition in an amount ranging from 0.01 to 5% by weight and preferably in an amount ranging from 0.5 to 2% by weight relative to the total weight of the composition.

The process for the manufacture of compound(I) follows the general scheme below:

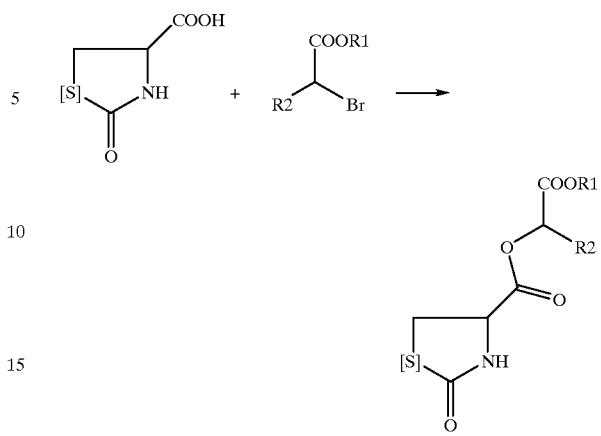

The detailed procedure is given below.

20 millimol of L-2-oxothiazolidine-4-carboxylic acid in 30 ml of anhydrous dimethylformamide are introduced into a 100 ml reactor with stirring. 10 mmol of $K_2CO_3$ are added and the mixture is heated for 20 minutes at 90° C. 22 mmol of α-bromo ester are then added. The mixture is heated at 80° C. for one to 4 hours depending on the case, until the starting materials have completely disappeared, with monitoring by thin layer chromatography. The reaction mixture is next cooled and then filtered to remove the salts. The filtrate is poured into 120 ml of water saturated with NaCl and is extracted 3 times with 100 ml of dichloromethane. The organic phases are combined and then washed with water. The organic phase is finally dried over sodium sulphate and then evaporated to dryness. The oil obtained is purified by chromatography on a column of silica, eluting with dichloromethane.

Various compounds are obtained according to the nature of the bromo ester used.

Compound 1: 2-oxothiazolidine-4-carboxylic acid 1-ethoxycarbonyl ethyl ester—R=ethyl and R2 methyl

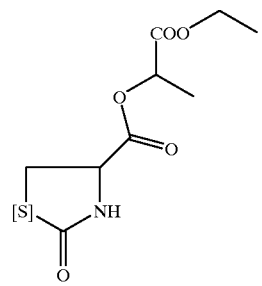

The product is in oily form and has a $^1$H NMR spectrum in accordance with the expected structure.

| Elemental analysis: | | | | | |
|---|---|---|---|---|---|
| | C | H | N | O | S |
| Theoretical | 43.72 | 5.30 | 5.66 | 32.35 | 12.97 |
| Calculated | 43.92 | 5.40 | 5.62 | 32.66 | 13.01 |

Compound 2: 2-oxothiazolidine-4-carboxylic acid 1-ethoxycarbonyl methyl ester—R1=ethyl and R2=H

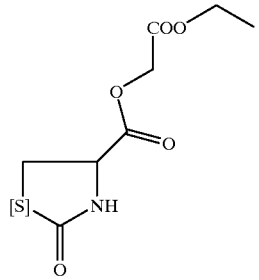

The product is in oily form and has a H$^1$ NMR spectrum in accordance with the expected structure.

Elemental analysis:

|  | C | H | N | O | S |
|---|---|---|---|---|---|
| Theoretical | 41.20 | 4.75 | 6.01 | 34.30 | 13.75 |
| Calculated | 40.87 | 4.76 | 5.98 | 34.81 | 13.76 |

Compound 3: 2-oxothiazolidine-4-carboxylic acid 1-ethoxycarbonyl butyl ester—R1=ethyl and R2=propyl

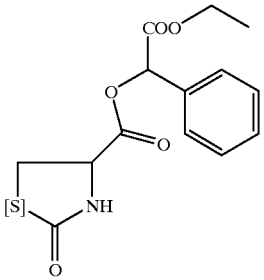

The product is in oily form and has a $^1$H NMR spectrum in accordance with the expected structure.

Elemental analysis:

|  | C | H | N | O | S |
|---|---|---|---|---|---|
| Theoretical | 47.99 | 6.22 | 5.09 | 29.06 | 11.65 |
| Calculated | 47.90 | 6.27 | 5.12 | 29.21 | 11.40 |

Compound 4: 2-oxothiazolidine-4-carboxylic acid 1-ethoxy-carbonyl phenyl methyl ester—R1=ethyl and R2=phenyl

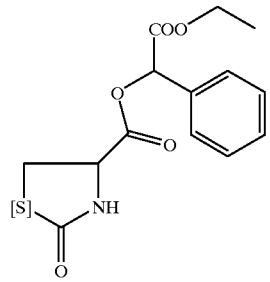

The product is in oily form. The $^1$H NMR spectrum is in accordance with the expected structure.

Elemental analysis:

|  | C | H | N | O | S |
|---|---|---|---|---|---|
| Theoretical | 54.36 | 4.89 | 4.53 | 25.86 | 10.37 |
| Calculated | 54.40 | 4.89 | 4.51 | 26.05 | 10.31 |

Compound 5: 2-oxothiazolidine-4-carboxylic acid 1-ethoxycarbonyl tridecyl ester—R1=ethyl and R2=dodecyl

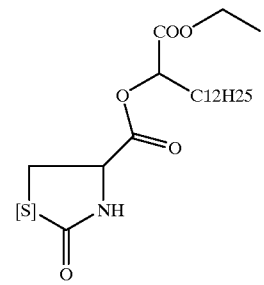

The product is in oily form and has a $^1$H NMR spectrum in accordance with the expected structure.

Elemental analysis:

|  | C | H | N | O | S |
|---|---|---|---|---|---|
| Theoretical | 59.82 | 8.79 | 3.49 | 19.92 | 7.98 |
| Calculated | 59.79 | 8.75 | 3.50 | 20.01 | 8.07 |

Compound 6: 2-oxothiazolidine-4-carboxylic acid 1-benzyloxycarbonyl ethyl ester—R1=benzyl and R2=methyl

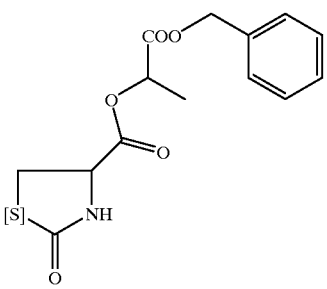

The product is in oily form and has a $^1$H NMR spectrum in accordance with the expected structure.

| Elemental analysis: | | | | | |
|---|---|---|---|---|---|
| | C | H | N | O | S |
| Theoretical | 54.36 | 4.89 | 4.53 | 25.86 | 10.37 |

Having generally described this invention, a further understanding can be obtained by reference to certain specific examples which are provided herein for purposes of illustration only and are not intended to be limiting unless otherwise specified.

The invention is illustrated in greater detail with the aid of the examples which follow. These various compositions are prepared according to the standard techniques.

The concentrations are given as a percentage by weight relative to the total weight of the composition.

EXAMPLE 1

Protective care cream

| | |
|---|---|
| 2-Oxothiazolidine-4-carboxylic acid 1-ethoxycarbonyl ethyl ester (compound 1) | 1 |
| Oxyethylenated polyethylene glycol 50 | 3 |
| Glyceryl mono di-stearate | 3 |
| Liquid petrolatum | 24 |
| Cetyl alcohol | 5 |
| Waters | qs 100 |

EXAMPLE 2

Bodycare cream

| | |
|---|---|
| 2-Oxothiazolidine-4-carboxylic acid ethoxycarbonyl ester (compound 1) | 0.5 |
| Sipol wax | 6 |
| Glyceryl monostearate | 1.5 |
| Sodium stearate | 0.8 |
| Liquid petrolatum | 6 |
| Isopropyl palmitate | 2 |
| Glycerol | 15 |
| Fragrance | 0.3 |
| Water | qs 100 |

EXAMPLE 3

Bleaching care cream

| | |
|---|---|
| 2-Oxothiazolidine-4-carboxylic acid ethoxycarbonyl ethyl ester (compound 1) | 0.5 |
| Jojoba oil | 13 |
| Alkyl paraben | 0.05 |
| Potassium sorbate | 0.3 |
| Cyclopentadimethylsiloxane | 10 |
| Stearyl alcohol | 1 |
| Stearic acid | 4 |
| Polyethylene glycol stearate | 3 |
| Vitamin E | 1 |
| Glycerol | 3 |
| Water | qs 100 |

The disclosure of France priority patent application 95-15334, filed Dec. 22, 1995, is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. An L-2-oxothiazolidine-4-carboxylic acid ester compound of the formula (I):

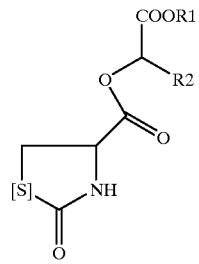

wherein:
R1 is
(a) hydrogen; or
(b) benzyl, which is unsubstituted or substituted by —Cl, —F, —OH, —COOH or —OR3, where R3 is selected from the group consisting of C1 to C18 alkyl, and benzyl; or
(c) saturated linear, unsaturated linear or branched C1–C8 alkyl groups which are unsubstituted or substituted by —Cl, —F, —OH, —COOH or —OR3, where R3 is selected from the group consisting of C1 to C18 alkyl, and benzyl; and R2 is
(a) hydrogen; or
(b) benzyl, which is unsubstituted or substituted by —Cl, —F, —OH, —COOH or —OR3, where R3 is selected from the group consisting of C1 to C18 alkyl, and benzyl; or
(c) saturated linear, unsaturated linear or branched C1–C24 alkyl groups which are unsubstituted or substituted by —Cl, —F, —OH, —COOH or —OR3, where R3 is selected from the group consisting of C1 to C18 alkyl, and benzyl; or
(d) phenyl.

2. The compound of claim 1, wherein R1 is a saturated linear alkyl group having from 1 to 4 carbon atoms.

3. The compound of claim 1, wherein R1 is ethyl or benzyl.

4. The compound of claim 1, wherein R2 is methyl, propyl, dodecyl, benzyl or hydrogen.

5. The compound of claim 1, which is selected from the group consisting of 2-oxothiazolidine-4-carboxylic acid 1-ethoxycarbonyl ethyl ester, 2-oxothiazolidine-4-carboxylic acid 1-ethoxycarbonyl methyl ester, 2-oxothiazolidine-4-carboxylic acid 1-ethoxycarbonyl butyl ester, 2-oxothiazolidine-4-carboxylic acid 1-ethoxycarbonyl phenyl methyl ester, 2-oxothiazolidine-4-carboxylic acid 1-ethoxycarbonyl tridecyl ester and 2-oxothiazolidine-4-carboxylic acid 1-benzyloxycarbonyl ethyl ester.

6. A cosmetic or dermatological composition or both, comprising at least one compound of claim 1, and a cosmetically or dermatologically acceptable carrier.

7. The composition of claim 6, further comprising at least one additive selected from the group consisting of fatty substances, preserving agents, vitamins, gelling agents, fragrances, silicones, surfactants, water, antioxidants, fillers and screening agents.

8. The composition of claim 7, wherein the fatty substances in an oil or wax or a mixture thereof.

9. The composition of claim 7, wherein the surfactant is glycerol mono di-stearate or sodium stearate.

10. The composition of claim 7, wherein the gelling agent is polyethylene glycol.

11. The composition of claim 7, wherein the compound is present in an amount ranging from 0.01 to 10% by weight relative to the total weight of the composition.

12. The composition of claim 11, wherein the compound is present in an amount ranging from 0.5 to 5% by weight relative to the total weight of the composition.

13. The composition of claim 7, wherein the additive is present in an amount ranging from 0.01 to 5% by weight relative to the total weight of the composition.

14. A process of depigmenting mammalian skin, comprising applying to the skin one or more compounds of claim 1, in a cosmetically or dermatologically acceptable carrier.

15. A process for manufacturing the compound of claim 1, comprising:

a) mixing L-2-oxothiazolidine-4-carboxylic acid with an α-bromoester having the formula:

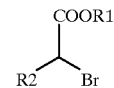

wherein R1 and R2 are as defined in claim 1, in the presence of a molar equivalent of a base; and b) heating the reaction mixture and then cooling and filtering the same.

16. The process of claim 15, which further comprises extracting, drying and purifying organic phases thereof.

17. The process of claim 15, wherein said reaction mixture is heated at a temperature and for a time sufficient such that all starting materials are reacted.

* * * * *

UNITED STATES PATENT AND TRADEMARK OFFICE
CERTIFICATE OF CORRECTION

PATENT NO.   : 6,004,543  
DATED        : December 21, 1999  
INVENTOR(S)  : Jean-Baptiste Galey Page 1 of 1

It is certified that error appears in the above-identified patent and that said Letters Patent is hereby corrected as shown below:

Column 5,  
Lines 36-49, delete  " 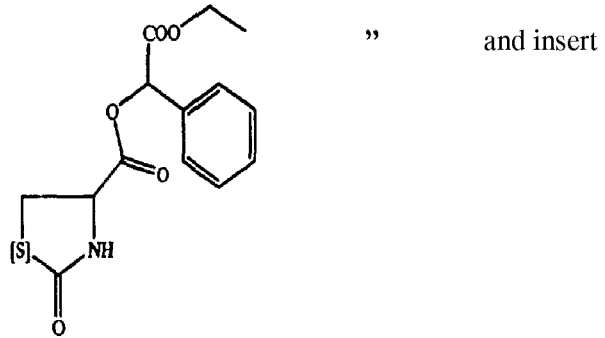 "  and insert therefor

-- 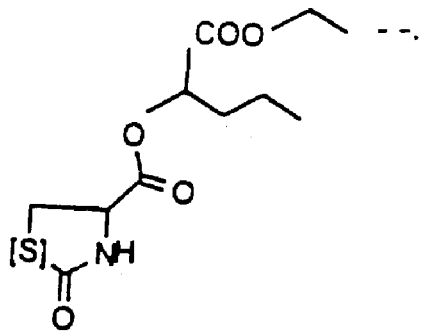 --.

Signed and Sealed this

Eleventh Day of June, 2002

Attest:

Attesting Officer

JAMES E. ROGAN  
*Director of the United States Patent and Trademark Office*